United States Patent [19]

Crawford et al.

[11] Patent Number: 5,403,584
[45] Date of Patent: Apr. 4, 1995

[54] USE OF STREPTOMYCES WYEC 108 TO CONTROL PLANT PATHOGENS

[75] Inventors: Donald L. Crawford, Moscow, Id.; Hyung W. Suh, Seoul, Rep. of Korea

[73] Assignee: Idaho Research Foundation, Inc., Moscow, Id.

[21] Appl. No.: 85,448

[22] Filed: Jun. 30, 1993

[51] Int. Cl.$^6$ .................. C12N 7/00; A01N 63/00; A61K 37/00; C10H 21/16
[52] U.S. Cl. .................. 424/93.43; 435/253.5; 47/57.6
[58] Field of Search .................. 424/93 G, 93 R, 93.1, 424/93.2, 93.4, 93.43; 47/57.601, 57.605, 57.612, 57.614, 57.618, 57.6; 435/252.35, 253.5

[56] References Cited

U.S. PATENT DOCUMENTS 3,160,560 12/1964 De Boer et al. .................. 435/77
4,053,627 10/1977 Scher .................. 424/278
4,534,965 8/1985 Brown et al. .................. 424/93.43
4,668,512 5/1987 Lewis et al. .................. 424/93

FOREIGN PATENT DOCUMENTS 676933 8/1966 Belgium .
2524486 10/1983 France .
WO93/18135 9/1993 WIPO .

OTHER PUBLICATIONS

M-L. Lahdenperä, "The Control of Fusarium Wilt on Carnation with a Streptomyces Preparation," Acta Horticulturae 216:85–92 (1987).
Ames, "Mycorrhiza development in onion in response to inoculation with chitin-decomposing actinomycetes," New Phytol. 112:423–427 (1989).
Bolton, "Effects of Amending Soilless Growing Mixtures With Soil Containing Antagonistic Organisms on Root Rot and Blackleg of Geranium (Pelargonium Hortorum) Caused by Phythium Splendens," Can. J. Plant Sci. 58:379–383 (Apr. 1978).
Bolton, "Control of *Pythium aphanidermatum* in pointsettia in a soilless culture by *Trichoderma viride* and a Streptomyes sp.," Canadian Journal of Plant Pathology 2:93–95 (1980).
Broadbent et al., "Bacteria dn Actinoymcetes Antagonistic to Fungal Root Pathogens in Australian Soils," Aust. J. Biol. Sci. 24:925–44 (1971).
Chambers and Millington, "Studies on Fusarium Species Associated with a Field Planting of 'Pathogen-tested' Potatoes," Aust. J. Agric. Res. 25:293–7 (1974).
Chibata and Tosa, "Use of Immobilized Cells," Ann. Rev. Biophys. Bioeng. 10:197–216 (1981).
DeFrank and Putnam, "Screening Procedures to Identify Soil-Borne Actinomycetes That Can Produce Herbicidal Compounds," Weed Science 33:271–274 (1985).
Filonow and Lockwood, "Evaluation of Several Actinomycetes and the Fungus *Hyphochytrium catenoides* of Biocontrol Agents for Phytophthora Root Rot of Soybean," Plant Disease, vol. 69, No. 12, pp. 1033–1036 (1985).
Fravel et al., "Encapsulation of Potential Biocontrol Agents in an Alginate-Clay Matrix," Phytopathology, vol. 75, No. 7, pp. 774–777 (1985).
Hussain et al., "Biological Control of Macrophomina phaseolina Charcoal Rot of Sunflower and Mung Bean," J. Phytopathology 130:157–160 (1990).
Lahdenpera et al., "Mycostop—A Novel Biofungicide Based on Streptomyces Bacteria," published prior to 1991.
Liljeroth et al., "Assimilate Translocation to the Rhizosphere of Two Wheat Lines and Subsequent Utilization (List continued on next page.)

Primary Examiner—David T. Fox
Assistant Examiner—Erich Veitenheimer
Attorney, Agent, or Firm—Klarquist Sparkman Campbell Leigh & Whinston

[57] ABSTRACT

This invention relates to a biocontrol formulation suitable for reducing the susceptibility of plants to fungal phytopathogens. In one aspect of the invention, a newly isolated strain of Streptomyces, Streptomyces WYEC 108, is incorporated into a suitable delivery medium and applied to plant seeds or plant roots.

20 Claims, No Drawings

OTHER PUBLICATIONS by Rhizosphere Microorganisms at Two Soil Nitrogen Concentrations," Soil Biol. Biochem., vol. 22, No. 8, pp. 1015–1021 (1990).

Lingappa and Lockwood, "Chitin Media for Selective Isolation and Culture of Actinomycetes," Phytopathology 52:317–323 (1962).

Lynch et al., "Prospects for control of Pythium damping–off of lettuce with Trichoderma, Gliocladium, and Enterobacter spp.," Biol. Fertil. Soils 11:1–5 (1991).

Merriman et al., "Effect of Bacillus and Streptomyces spp. Applied to Seed," in E. Bruehl (ed.), Biology & Control of Soil–Borne Plant Pathogens, pp. 130–133 (1977).

Meyer and Linderman, "Selective Influence on Populations of Rhizosphere or Rhizoplane Bacteria and Actinomycetes by Mycorrhizas Formed by *Glomus Fasciculatum*," Soil Biol. Biochem., Vol. 18, No. 2, pp. 191–196 (1986).

Miller et al., "Variation and composition of bacterial populations in the rhizospheres of maize, wheat, and grass cultivars," Can. J. Microbiol. 35:656–660 (1989).

Miller et al., "Fluctuations in the fluorescent pseudomonad and actinomycete populations of rhizosphere and rhizoplane during the growth of spring wheat," Can. J. Microbiol. 36:254–258 (1990).

Miller et al., "The Dynamics of Actinomycetes and Fluorescent Pseudomonads in Wheat Rhizoplane and Rhizosphere," Symbiosis 9:389–391 (1990).

Mohamed, "Physiological and Antagonistic Activities of Streptomycetes in Rhizosphere of Some Plants," Egypt. J. Phytopathol. 14:121–128 (1982).

Panosyan et al., "The Nature of Physiologically Active Substances of Actinomycetes and the Effect of Their Metabolites on Plant Growth," Plant Microbe Relationships, pp. 241–245 (1965).

Reddi and Rao, "Antagonism of Soil Actinomycetes to Some Soil–Borne Plant Pathogenic Fungi," Indian Phytopathology, vol. 24, pp. 649–657 (1971).

Scrinivasan et al., "Physiology and nutritional aspects of actinomycetes: an overview," World Journal of Microbiology and Biotechnology 7:171–184 (1991).

Singh and Mehrota, "Biological Control of *Rhizoctonia Bataticola* on Gram by Coating Seed with Bacillus and Streptomyces spp. and their Influence on Plant Growth," Plant and Soil 56:475–483 (1980).

Stevenson, "Antibiotic Activity of Actinomycetes in Soil as Demonstrated by Direct Observation Techniques," J. Gen. Microbiol. 15:372–380 (1956).

Suh et al., "Production of antifungal metabolites by Streptomyces WYEC 108," Abstract, Society for Industrial Microbiology 49th Annual Meeting (Jul. 1992).

Sutherland and Papavizas, "Evaluation of Oospore Hyperparasites for the Control of Phytophthora Crown Rot of Pepper," J. Phytopathology 131:33–39 (1991).

Tahvonen, "Preliminary experiments into the use of Streptomyces spp. isolated from peat in the biological control of soil and seed–borne diseases in peat culture," Journal of the Scientific Agricultural Society of Finland 54:357–369 (1982).

Tahvonen and Avikainen, "The biological control of seed–borne *Alternaria brassicicola* of cruciferous plants with a powdery preparation of Streptomyces sp.," Journal of Agricultural Science in Finland 59:199–207 (1987).

Tu, "Hyperparasitism of *Streptomyces albus* on a Destructive Mycoparasite *Nectria inventa*," J. Phytopathology 117:71–76 (1986).

Turhan, "A new race of Streptomyces ochraceiscleroticus in the biological control of some soil–borne plant pathogens," Journal of Plant Diseases and Protection 88(7):422–434 (1981).

Turhan and Turhan, "Suppression of Damping–off on Pepper Caused by *Pythium ultimum* Trow and *Rhizoctonia solani* Kühn by Some New Antagonists in Comparison with *Trichoderma harzianum* Rifai," J. Phytopathology 126:175–182 (1989).

Walker and Connick, Jr., "Sodium Alginate for Production and Formulation of Mycoherbicides," Weed Science 31:333–338 (1983).

Williams, "Are antibiotics produced in soil?," Pedobiologia 23:427–435 (1982).

Zuberer et al., "Populations of bacteria and actinomycetes associated with sclerotia of *Phymatotrichum omnivorum* buried in Houston black clay," Plant and Soil 112:69–76 (1988).

Sabaou and Bounaga, "Actinomycetes parasites de champignons: etude des especes, specificite de l'action parasitaire au genre Fusarium et antagonisme dansn le sol envers *Fusarium oxysporum* f.sp. albedinis (Killian et Maire) Gordon," Can. J. Microbiol. 33:445–451 (1987) English summary only.

Tahvonen, "Mycostop—ett biologiskt bekampningsmedel mot svampsjukdomar" (Mycostop, biological formulation for control of fungal diseases), Växtskyddsnotiser 49:5, 86–90 (1985), English summary only.

2

USE OF STREPTOMYCES WYEC 108 TO CONTROL PLANT PATHOGENS

FIELD OF THE INVENTION

The present invention relates to a new strain of Streptomyces bacteria that is capable of inhibiting the growth of soil borne plant pathogens and enhancing plant growth.

BACKGROUND OF THE INVENTION

Fungal phytopathogens are a cause of severe economic losses in the agricultural and horticultural industries. Many different types of fungal phytopathogens have been described: these pathogens cause plant diseases such as damping-off, white-rot, brown-rot and root-rot. Such diseases can kill emerging seedlings, reduce plant vigor and adversely affect crop yields.

To minimize fungal infections, bedding-plant nurseries may grow seedlings in steam sterilized or chemically treated soils. However, such treatments also remove beneficial microorganisms from the soil, including microorganisms that would normally compete with soil fungi. In such cases, if a fungal pathogen is accidentally introduced, it may spread rapidly and produce widespread disease.

In agricultural settings, soils infested with phytopathogenic fungi may be unsuitable for growing certain crops. For example, soybean production in Michigan and in other soybean growing states is often severely limited by Phytophthora root rot caused by the fungus *Phytophera megasperma* (Filinow and Lockwood, 1985). Species of Pythium fungi are widespread in soils in parts of California, Washington State and Idaho. *Pythium ultimum* is the most common pathogenic species encountered and is associated with pre- and post-emergence damping-off of seedlings. This species is a serious pathogen of wheat, peas and chickpeas and other crop plants grown in these soils and in soils in other states and other countries (Trapero-Casas et al., 1990; Stanghellini and Hancock, 1970; Kraft and Burke, 1971; Westerlund et al., 1988). The use of chemical agents to control fungal phytopathogens is often not practical due to high costs, lack of efficacy and the emergence of resistant strains of the fungi. Additionally, the use of chemical fungicides is not desirable from an environmental viewpoint.

It is an object of the present invention to provide a biological control means of reducing fungal pathogen infection of plants.

SUMMARY OF THE INVENTION

The foregoing object has been achieved by the isolation of a number of actinomycete bacteria that are shown to be effective in inhibiting the growth of fungal phytopathogens. In particular, one of the isolated actinomycete bacteria, herein named Streptomyces WYEC 108, is shown to exhibit strong antagonism towards a wide range of fungal plant pathogens, including pathogens that cause the plant diseases commonly known as damping-off, root rot, white rot and brown rot. Thus, one aspect of the present invention is a biologically pure culture of Streptomyces WYEC 108.

The present invention also sets forth various compositions suitable for treating plant seeds or plant roots with Streptomyces WYEC 108. Such compositions are useful to reduce the susceptibility of plants to fungal infection and to enhance the growth of treated plants. In a preferred embodiment, such compositions comprise a biologically pure culture of Streptomyces WYEC 108 and a delivery medium. In particular embodiments, the delivery medium may comprise alginate gel, peat moss, sand or cornmeal. In one embodiment, the present invention encompasses a delivery medium which comprises peat moss, sand and cornmeal together with Streptomyces WYEC 108. In another embodiment, the delivery medium comprises at least $10^5$ colony forming units per gram of delivery medium.

In another embodiment, the present invention encompasses alginate gel pellets containing Streptomyces WYEC 108. Such pellets can be added directly to the roots of growing plants or to horticultural or agricultural soils to reduce damage to plants caused by phytopathogenic fungi.

The present invention also encompasses methods for reducing the susceptibility of a plant to fungal infection. In one embodiment, this method comprises delivering Streptomyces WYEC 108 to the roots of a plant. In another embodiment, the method comprises immersing seeds in a composition that contains Streptomyces WYEC 108 and thereafter planting the coated seeds in a suitable growth medium. In this method, a suitable composition comprises alginate gel containing Streptomyces WYEC 108.

DETAILED DESCRIPTION OF THE INVENTION

The present invention describes the isolation of a number of actinomycete strains from soils. A number of these strains are shown to be effective in reducing the effects of fungal pathogens on plants, including lettuce, chickpea and pepper. In particular, the present invention sets forth the isolation of a strain herein referred to as Streptomyces WYEC 108. Strain WYEC 108 is shown to exhibit strong antagonism towards a wide range of fungal phytopathogens, including pathogens that cause pre- and post-emergence damping off of seedlings, root rot, brown rot and white rot. As such, strain WYEC 108 is particularly suitable as a biocontrol agent that can be used to protect plants against infection by these phytopathogens. Thus, Streptomyces WYEC 108 is useful in methods for reducing the susceptibility of plants to fungal infection. As such, plants treated with Streptomyces WYEC 108 will show reduced effects of fungal infection. Fungal infection of susceptible untreated plants affects certain growth characteristics of such plants. For instance, untreated plants exposed to fungal pathogens may show significant reductions in plant height, plant biomass and crop yield compared to plants not exposed to the fungal pathogen. In preferred embodiments of the present of the invention, plants treated with Streptomyces WYEC 108 and subsequently exposed to the fungal pathogen will show less severe reductions in plant height, plant biomass and crop yield than untreated plants exposed to the fungal pathogen. In more preferred embodiments, plants treated with Streptomyces WYEC and exposed to the fungal pathogen will show growth characteristics similar to the untreated, unexposed plants. In most preferred embodiments, plants treated with Streptomyces WYEC 108 and exposed to the fungal pathogen will show growth characteristics superior to the untreated, unexposed plants.

Strain WYEC 108 colonizes plant roots in the presence of competition from rhizospere microflora. Strain WYEC 108 is shown to enhance the growth of lettuce plants growing in steam sterilized soil and pepper plants growing in an agricultural field.

Also encompassed by this invention are means of producing vegetative cells or spores of strain WYEC 108 suitable for incorporation into a delivery medium. The composition comprising the vegetative cells and spores of WYEC 108 and the delivery medium is shown to have a long shelf life and to be suitable for delivering strain WYEC 108 to plants.

Materials and Methods

Bacterial Growth Media

All bacterial growth media were prepared using distilled water and sterilized by autoclaving prior to use. All bacterial samples were handled using standard aseptic laboratory techniques to maintain purity.

YGM (yeast extract/glucose/mineral salts) medium comprised 0.6% (wt/vol) yeast extract (Difco Laboratories, Detroit, Mich.), 1.0% (wt/vol) glucose, and phosphate mineral salt solution (5.3 g of $Na_2HPO_4$, 1.98 g of $KH_2PO_4$, 0.2 g of $MgSO_4.7H_2O$, 0.2 g of NaCl, 0.05 g $CaCl_2.2H_2O$, plus 1.0 ml of trace elements (Pridham and Gottlieb, 1948) per liter of deionized $H_2O$; pH 7.1 to 7.2). The solution of trace elements consisted of 0.64 g of $CuSO_45H_2O$, 0.11 g of $FeSO_4.7H_2O$, 0.79 g of $MnCl_2.4H_2O$, 0.15 g of $ZnSO_4.7H_2O$ in 100 ml of distilled water.

WYE (water/yeast extract/agar) medium, modified from Reddi and Rao (1971) contained yeast extract (Oxoid, 0.25 g/l) as the sole carbon and nitrogen source, and agar (Oxoid, 18.0 g/l). The medium was buffered to pH 7.2–7.4 with $K_2HPO_4$ (0.5 g/l).

WYEC (water/yeast extract/cellulose/agar) was WYE agar to which a thin overlay agar was added. The overlay agar contained 0.25 g/l of cellulose (Solka Floc, Sigma Chemical Co.) and 18,0 g/l agar in distilled water.

CYD (casamino acids/yeast extract/dextrose agar) medium contained casamino acids (Difco: 0.5 g/l), yeast extract (Oxoid or Difco: 0.8 g/l), D-glucose (0.4 g/l), $K_2HPO_4$ (2.0 g/l; pH 7.2–7.4), and 18.0 g/l agar in distilled water.

YCED (casamino acids/yeast extract/dextrose/agar; modified from Reddi and Rao (1971) contained yeast extract (Oxoid, 0.3 g/l), casamino acids (Difco, 0.3 g/l), D-glucose (0.3 g/l), and agar (Oxoid, 18.0 g/l). The medium was buffered with $K_2HPO_4$ (2.0 g/l).

CYPC (cellulose/yeast extract/peptone/compost extract/agar) contained cellulose (Solka Flock, Sigma Chemical Col; 5.0 g/l), yeast extract (1.0 g/l), peptone (Oxoid, 1.0 g/l), phosphate buffer ($K_2HPO_4$, 0.75 g/l), agar (18.0 g/l), and compost extract (100 ml/l) replacing 100 ml of distilled water in the medium. It was poured directly and not used as an overlay agar.

MSSC (mineral salts/starch/casein/agar; Turhan, 1981) contained a mineral salts solution consisting of NaCl (2.0 g/l), $MgSO_417H_2O$ (0.05 g/l), $CaCO_3$ (0.02 g/l), $FeSO_418H_2O$ (0.01 g/l), and $KNO_3$ (2.0 g/l), plus organic constituents including soluble starch (10.0 g/l) and casein (0.3 g/l), plus agar (18.0 g/l). The medium was buffered with $K_2HPO_4$ (2.0 g/l).

Sporulation medium (ATCC Medium #5) contained yeast extract (1.0 g/l), beef extract (1.0 g/l), tryptose (2.0 g/l), $FeSO_4$ (0.01 g/l), glucose (10.0 g/l), and agar (15.0 g/l). The medium was adjusted to pH 7.2 prior to autoclaving. (17th Edition ATCC Catalogue of Bacteria and Bacteriophages).

CYG medium contained Casamino acids (acid hydrolysate) (5.0 g/l), yeast extract (5.0 g/l) and glucose (10.0 g/l) in distilled water, adjusted to pH 7.1–7.2.

Delivery medium (comprising sand/cornmeal/water or peat moss/sand/cornmeal in ratios as set forth below) was sterilized by steam sterilization prior to use. Sterilization was typically performed by autoclaving 3 times, each time by 90 minutes.

Harvesting of bacterial growth

For mycelial growth of Streptomyces WYEC 108, one liter Erlenmeyer flasks containing 500 ml YGM medium (pH 7.1–7.2), were inoculated with 20 ml of stock culture (prepared as described in Example II) and incubated with shaking at 250 rpm at 30° C. for three days. Mycelia were then harvested by centrifugation at 5,000 rpm for 10 minutes. Alternatively, mycelia were harvested by permitting the culture to stand until mycelia and spores settled to the bottom of the Erlenmeyer flask. Supernatant media was then decanted off and the concentrated suspension of mycelia and spores was used directly to inoculate delivery medium.

Cells and spores were also produced by growth on solid medium (for example sporulation agar). Mycelia and spores were harvested from sporulation agar by scraping the surface of the agar into distilled water. This suspension of conidiospores and mycelia was then mixed directly into the delivery medium.

For the production of spores of Streptomyces WYEC 108 two liter Erlenmeyer flasks containing 1,200 ml YGM medium were each inoculated with 50 ml of stock culture and incubated with shaking at 250 rpm at 30° C. for 12–18 days. Spores were harvested by centrifugation at 9,000 rpm for 10 minutes.

Fungal Pathogens

*Pythium ultimum* PuMXL was obtained from the culture collection of the Department of Microbiology and Crop Protection at Horticulture Research International, Worthing Road, Littlehampton, West Sussex BN17 6LP, United Kingdom. White-rot fungi *Phanerochaete chrysosporium* and *Coriolus versicolor;* brown-rot fungi *Postia placenta, Caldariomyces rumago*, and *Gloeophyllum trabeum;* soil born fungal pathogens *Rhizoctonia solani, Fusarium sambucinctum, Geotrichum candidum*, and *Verticillium dahliae* came from the culture collection of professor Don L. Crawford, Department of Bacteriology, University of Idaho, Moscow, Id. *Phthium irregulare, Phytophthora capsici, Phytophthora cinnamomi, Phytophthora parasitica, Sclerotinia cepivorum*, and *Sclerotinia sclerotiorum* came from the culture collection of Dr. Wesley Chun, Department of Plant Soil Entomology Science, University of Idaho, Moscow, Id. *Fusarium oxysporum* came from the culture collection of Dr. Arthur D. Partridge, Department of Forest Resources, University of Idaho, Moscow, Id. All cultures were maintained on potato dextrose agar or corn meal agar and grown at 25° C. These strains were identified as "pathogens" when obtained, but were not retested for their pathogenicity.

Bioassay Soil

For use in bioassays, soil naturally infested with *Pythium ultimum* was collected from several sites in the Palouse region near Moscow, Id. This soil was collected from the top 15 cm from fields that had been cropped with wheat and pea in the previous two seasons. The soil population of Pythium species was determined as follows: A soil dilution of 1.0 g air-dried soil in 50 ml sterilized distilled-water was thoroughly mixed with a Vortex tube mixer. A 0.1 ml sample of the well mixed dilution was placed as small droplets on 3-day-old 2% water agar plates (Stanghellini and Hancock, 1970). Plates were incubated at 25° C. and read periodically using a low power (×10) dissecting microscope with fluorescent illumination to determine the identity and numbers of Pythium species present. Colonies on each plate were checked after 12, 48 and 72 hours of incubation, before the final population was estimated. Identification was based upon the morphological characteristics of fungal mycelium of Pythium species under microscope and the growth pattern on 2% (w/v) water agar plates. Fungal colonies of a pure culture growing on 2% (w/v) water agar served as a control for visual identification purposes (Stanghellini and Hancock, 1970; Stasz et al., 1980).

Examination of this soil indicated that the population densities of *P. ultimum* and *P. irregulare* were 354 ±15 and 194 ±11 cfu/g of air-dried soil at the time of seeding (Spring, 1992), respectively. Population density of other Pythium species was 57 ±9 cfu/g of air-dried soil. *P. ultimum* and *P. irregulare* were the most prevalent species isolated from the collected soil.

EXAMPLE I

Isolation of Actinomycete Strains Exhibiting Antagonism Towards Fungal Phytopathogens Actinomycete strains were isolated from four rhizosphere-associated and four non-rhizosphere-associated soil samples. These strains were then tested for utility as inhibitors of fungal phytopathogens.

Isolation of Actinomycetes

Actinomycete isolates were isolated from 8 different soils by serial-dilution/spread-plate technique. Dilutions ($10^{-5}$ to $10^{-7}$) were plated onto various agar isolation media. The composition of these media is set forth in "Materials and Methods" above. Actinomycete isolates were designated according to the isolation medium on which they were isolated. For example, WYEC 108 was isolated on WYEC medium and YCED 9 was isolated on YCED medium. In general, such media are poor in organic carbon, which effectively controls eubacterial and fungal growth and aids in isolating the slower growing actinomycetes. Since WYE and YCED agars were particularly effective isolation media, they were used predominantly. Dilution plates were incubated at 25° C. for 4 to 10 days to allow the actinomycetes to sporulate, and then colonies were picked and streaked onto WYE or YCED agar plates for purification. Pure colonies were transferred from these plates to YCED agar slants or CYD agar slants, incubated at 25° C. or 37° C. until sporulated, and stored at 5° C. until used. Stock cultures were transferred every 3 to 4 weeks.

Soils (i) Non-rhizosphere-associated soils.

Samples (100 to 200 g) of soil were taken from the top 7.5 to 10 cm of the soil profile at 4 sites in the United Kingdom, including a cultivated rose garden (Soil S1) in Rustington, West Sussex; between rows in a wheat field (Soil S2) at the Horticulture Research International (H.R.I.) farm in Littlehampton, West Sussex; a forest soil (Soil S6) from the Wynd Cliff hardwood forest reserve, South Wales; and a grassland (Soil S7) sometimes grazed by sheep at Hastings Hill, South Downs, West Sussex. These soils were considered non-rhizospheric, although they did contain plant roots in varying amounts.

(ii) Rhizosphere-associated soils.

Rhizosphere-associated soil samples from 4 places were prepared essentially by the method of Miller et al. (1990). Soil 3 (S3) was associated with the roots of a dandelion plant (*Taracum officinale*) in a rose garden at H.R.I. in West Sussex, England. Soil (S5) was associated with wheat roots and was taken from the same field as S2, a wheat field at the H.R.I.'s farm in Littlehampton, West Sussex. Soil 4 (S4) was also associated with wheat roots, but the soil was from a field on Bignor Hill along the South Downs Way, West Sussex. Soil 8 (S8) was associated with the roots of linseed plants and was taken from a field adjacent to the S7 sampling site, a grassland sometimes grazed by sheep at Hastings Hill, South Downs, West Sussex.

Actinomycetes isolated from the soils could be divided into those isolated from non-rhizosphere- (S1, S2, S6, and S7) or rhizosphere-associated (S3, S4, S5, and S8) soils. All soils were characterized for their moisture content by drying 3 g (wet weight) samples (three replicates) at 100° C. for 58 h and then reweighing them. Soil pH was determined by thoroughly mixing a 1:1 soil:water slurry, allowing the solids to settle for 2 h, and taking the pH of the supernatant solution. After collection, soils were stored at 4° C. until used (24 to 48 h). The isolates were confirmed to be actinomycete strains by visual examination which showed that the colonies formed by these strains were typical actinomycete colonies (hard and leathery with an aerial mycelium containing spores). Further confirmation of the identity of these strains as actinomycetes was obtained by microscopy.

Determination of pH range for growth.

Each actinomycete isolate was tested for its ability to grow at pH 5.5 to 8.0. Cultures were spot-inoculated onto plates of CYD agar, buffered to pH 5.5, 6.0, 6.5, 7.0, and 8.0 with combinations of $K_2HPO_4$ and $KH_2PO_4$ buffers at 100 mM concentration. The final pH of each medium was adjusted to its final value just prior to autoclaving. Cultures were checked for growth after 5 to 7 days incubation at 25° or 37° C. Plates were evaluated visually for little or no observable growth (±), some growth (+ or ++), or excellent growth (+++).

As shown in Table I, the rhizosphere-associated soils gave almost twice as many isolates as the non-rhizosphere-associated soils. Each isolate was tested for growth on CYD agar media ranging from pH 5.5 to pH 8.0. All isolates grew from pH to 6.5 to 8.0. Only 9 failed to grow at pH 6.0, while 57 (21%) failed to grow at pH 5.5. Of those that grew at pH 5.5, growth varied from poor to excellent depending upon the isolate. The ability of the isolates to sporulate strongly on CYD agar was also determined by visual and microscopic observation of colonies after 5-10 days of incubation.

TABLE I

| Soil | Soil pH | Selective medium | | Totals |
|---|---|---|---|---|
| | | YCED | WYE | |
| Non-rhizosphere-associated soils | | | | 77 |
| 1 | 7.5 | 8 | 16 | 24 |
| 2 | 5.4 | 5 | 6 | 11 |
| 6 | 7.2 | 20 | 8 | 28 |
| 7 | 7.4 | 13 | 1 | 14 |
| Rhizosphere-associated soils | | | | 140 |
| 3 | 7.0 | 17 | 22 | 39 |
| 4 | 7.6 | 32 | 33 | 65 |
| 5 | 6.5 | 11 | 15 | 26 |
| 8 | 7.3 | 8 | 2 | 10 |

TABLE I-continued

| Soil | Soil pH | Selective medium YCED | WYE | Totals |
|---|---|---|---|---|
| Total isolates | | 114 | 103 | 217 |

In Vitro Antagonism Assay

Eighty-two isolates were chosen on the basis of their ability to grow well and sporulate strongly on CYD agar.

To test the ability of these isolates to inhibit the growth of *P. ultimum*, an in vitro plate assay was used. Each actinomycete was streak-inoculated on corn meal agar (CMA) plates, to one side of center. The culture was incubated at 25° C. for about 8 days or until the culture had sporulated. A CMA agar block (0.5 cm²) containing actively growing *P. ultimum* mycelium was then aseptically placed in the center of the plate. Incubation was continued for 96 h. After 48 and 96 h the plate was examined for inhibition in the growth of *P. ultimum*. Inhibition was indicated when *P. ultimum* mycelial growth in the direction of the actinomycete colony was retarded or prevented. The results of this test are shown in Table II.

TABLE II

| Culture | Source (soil) | Growth at pH 5.5 (+ or −) | Antagonism observed[a] 48 hr | 96 hr |
|---|---|---|---|---|
| *Antagonistic (at 96 hr)* | | | | |
| WYEC 108 | 8 | + | +++ | +++ |
| YCED 1 | 1 | + | ++ | ++ |
| YCED 9 | 2 | + | +++ | +++ |
| YCED 35 | 4 | + | + | + |
| YCED 48 | 4 | + | + | + |
| YCED 95 | 7 | + | + | + |
| YCED 106 | 7 | + | ++ | +++ |
| WYE 21 | 4 | + | + | + |
| WYE 22 | 4 | + | + | + |
| WYE 30 | 4 | − | + | + |
| WYE 31 | 4 | + | + | + |
| WYE 78 | 1 | + | ++ | ++ |
| WYE 88 | 1 | + | + | + |
| WYE 90 | 6 | + | +++ | +++ |
| WYE 91 | 6 | + | +++ | +++ |
| WYE 97 | 1 | + | ++ | ++ |
| MSSC 1 | 2 | + | + | + |
| MSSC 2 | 2 | + | + | + |
| *Nonantagonistic (at 96 hr)* | | | | |
| WYE 6 | 1 | + | + | − |
| WYE 9 | 3 | + | − | − |
| WYE 11 | 3 | + | + | − |
| WYE 12 | 4 | + | + | − |
| WYE 13 | 4 | + | − | − |
| WYE 20 | 4 | + | − | − |
| WYE 23 | 3 | + | − | − |
| WYE 27 | 4 | − | − | − |
| WYE 28 | 3 | + | − | − |
| WYE 29 | 4 | + | + | ± |
| WYE 34 | 3 | + | − | − |
| WYE 35 | 3 | + | − | − |
| WYE 38 | 4 | + | − | − |
| WYE 42 | 3 | + | − | − |
| WYE 43 | 4 | + | − | − |
| WYE 45 | 3 | + | − | − |
| WYE 47 | 3 | + | − | − |
| WYE 53 | 4 | + | − | − |
| WYE 54 | 3 | + | − | − |
| WYE 56 | 3 | + | − | − |
| WYE 68 | 5 | + | − | − |
| WYE 69 | 6 | + | − | − |
| WYE 73 | 6 | + | − | − |
| WYE 75 | 2 | + | − | − |
| WYE 77 | 2 | + | ± | ± |
| WYE 84 | 2 | + | − | − |
| WYE 85 | 2 | + | − | − |
| WYE 93 | 1 | + | − | − |
| WYE 94 | 1 | + | − | − |
| WYE 120 | 8 | + | − | − |
| WYE 121 | 7 | + | − | − |
| YCED 11 | 1 | + | − | − |
| YCED 15 | 4 | + | − | − |
| YCED 16 | 4 | + | − | − |
| YCED 17 | 3 | + | − | − |
| YCED 25 | 4 | + | − | − |
| YCED 28 | 4 | + | − | − |
| YCED 29 | 3 | + | − | − |
| YCED 30 | 3 | + | − | − |
| YCED 31 | 3 | + | − | − |
| YCED 32 | 4 | + | ± | − |
| YCED 41 | 4 | + | − | − |
| YCED 44 | 4 | + | ± | − |
| YCED 54 | 4 | + | − | − |
| YCED 56 | 4 | + | − | − |
| YCED 62 | 5 | + | − | − |
| YCED 64 | 5 | − | − | − |
| YCED 71 | 5 | + | − | − |
| YCED 73 | 5 | + | − | − |
| YCED 85 | 6 | − | − | − |
| YCED 88 | 5 | + | − | − |
| YCED 93 | 7 | + | − | − |
| YCED 96 | 7 | + | − | − |
| YCED 98 | 8 | + | − | − |
| YCED 105 | 7 | + | − | − |
| WYEC 101 | 4 | + | − | − |
| WYEC 104 | 8 | + | − | − |
| WYEC 107 | 7 | − | ± | − |
| WYEC 111 | 8 | + | − | − |
| WYEC 113 | 8 | + | ± | ± |
| WYEC 116 | 8 | + | − | − |
| WYEC 118 | 7 | + | − | − |
| CYPC 2 | 6 | + | − | − |
| CYPC 5 | 6 | + | − | − |

[a]Inhibition of *P. ultimum* defined as hyphal growth less abundant and growth retarded slightly on area of plate to the side where the actinomycete had been grown.
+++ very strong inhibition with zone of inhibition ≧ 2.0 cm
++ strong inhibition with zone of inhibition ≧ 1.0 cm
+ growth definitely retarded, with obvious zone of inhibition near colony
± minor inhibition of *P. ultimum* (hyphal growth less abundant and growth retarded
− no inhibition After 96 hr, five isolates (WYEC108, YCED9, YWE91, WYE90, and YCED106) showed very strong antagonism towards *P. ultimum*, four (YCED1, YCED106, WYE97, and WYE98) showed strong antagonism, and ten others showed weak antagonism. The remaining isolates were either not antagonistic, or only very weakly so. The cultures that clearly inhibited growth of *P. ultimum* were about equally divided between those isolated from rhizosphere-associated soils and non-rhizosphere-associated soils.

Seventy of the isolates that grew at pH 5.5 were also tested for their in vitro antagonism against the white-rot fungus *Phanerochaete chrysosporium* on cornmeal agar (CMA). Thirteen of the isolates showed some degree of antagonism of the white-rot fungus as shown in Table III. The degree of antagonism varied from very strong (+++) to relatively weak (+) as defined by the size of the inhibition zone. Five of the cultures that showed antagonism against *P. chrysosporium* (WYEC108, WYE78, 2YE90, YCED9, and MSSC2) were further tested on CMA against an additional white-rot fungus (*Coriolus versicolor*) and two types of brown-rot fungi (*Postia placenta* and *Gloeophyllum trabeum*). Four isolates (MSSC2, YCED9, WYE90, WYEC108) showed very strong antagonism towards the above-mentioned white- and brown-rot fungi. One isolate, WYEC78, showed strong antagonism only against the two white-rot fungi.

TABLE III

| Culture | Source (soil) | Growth at pH 5.5 (+ or −) | Antagonism observed[a] | |
|---|---|---|---|---|
| | | | 48 hr | 96 hr |
| Antagonistic | | | | |
| WYEC 108[b] | 8 | + | +++ | +++ |
| WYE 22 | 4 | + | ++ | ++ |
| WYE 78[c] | 1 | + | + | + |
| WYE 90[b] | 6 | + | +++ | +++ |
| WYE 97 | 1 | + | ++ | ++ |
| YCED 9[b] | 2 | + | +++ | +++ |
| YCED 29 | 3 | + | + | + |
| YCED 41 | 4 | + | + | + |
| YCED 48 | 4 | + | + | + |
| YCED 95 | 7 | + | ++ | + |
| CYPC 2 | 6 | + | ++ | ++ |
| CYPC 5 | 6 | + | + | + |
| MSSC 2[b] | 2 | + | +++ | ++ |

[a]Inhibition of *P. ultimum* defined as hyphal growth less abundant and growth retarded slightly on area of plate to the side where the actinomycete had been grown.
+++ very strong inhibition with zone of inhibition ≧ 2.0 cm
++ strong inhibition with zone of inhibition ≧ 1.0 cm
+ growth definitely retarded, with obvious zone of inhibition near colony
± minor inhibition of *P. ultimum* (hyphal growth less abundant and growth retarded
− no inhibition
[b]Inhibition of *Coriolus versicolor, Postia placenta* and *Gloeophyllum trabeum* in addition to *P. chrysosporium*.
[c]Inhibition of *Postia placenta* and *Gloeophyllum trabeum* in addition to *P. chrysosporium*.

In Vivo Bioassay to Determine Activity of Actinomycete Isolates on Lettuce Seedlings The biocontrol assay procedure of Lynch et al. (1991, 1992) was used to assay 12 of the isolates for their effect on the germination and outgrowth of lettuce (*Latuca sativa*) seeds.

For control plants, 9-cm-diameter plastic pots were filled with lettuce potting mix and tamped down with a petri dish. Ten lettuce seeds were placed on top, lightly pressed into the potting mix, and lightly covered with loose mix. The pots were then placed on trays in a bed of water, and incubated in the dark at 20° to 22° C. until germination was evident (approximately 3 days). The trays were then transferred to a capillary matting in a greenhouse maintained at 15° to 25° C. and watered as required. The numbers of germinated seedlings in each pot were counted periodically for up to 18 days.

For plants treated with the actinomycete isolates, pots were filled with potting mix inoculated with the spores of a specific actinomycete. Potting mix was inoculated with spores from CYD stock slants, to an average level of $10^8$ to $10^9$ cfu/g (dry weight) of potting mix. Cfu/g of potting mix was determined by viable counts on CYD agar plates at the time of inoculation. Lettuce seeds were then planted as above, covered with a small amount of inoculated potting mix, and thereafter treated similarly to controls.

For plants treated with a specific actinomycete and the damping-off fungus *Pythium ultimum* (strain PuMXL, Lynch et al., 1991), the mix was also inoculated with the fungal pathogen at ca. 200 sporangia/g (dry weight) of mix. The procedure of Lynch et al. (1991, 1992) was used to produce the pathogen sporangia and inoculate the potting mix. Sporangial counts were made with a haemocytometer, and the pathogenicity of the *P. ultimum* strain was confirmed before use by passage through lettuce.

In all treatments, pots were prepared in replicates of five. In the glasshouse, pots were set in a random block arrangement surrounded by "guard plants"; guard plants served to provide uniformity of conditions and to act as a buffer. Eighteen days after planting, the plants were harvested, the emergence of the final stand was measured, and wet and dry weights (aboveground leaves and stem) were determined. Plant wet and dry weights were recorded as total mg biomass per pot, and as average mg biomass per plant. Values were reported as averages of the five replicates ±standard deviation. Thus, each value was based upon 50 seeds planted per treatment (five replicate pots planed with 10 seeds each). Percent seed germination and final plant stand values were calculated similarly.

TABLE IV

| Actino-mycete strain | Concentration × $10^5$ cfu g$^{-1}$ dry compost | Number of Healthy plants per pot (n) | | Shoot weight | | | |
|---|---|---|---|---|---|---|---|
| | | | | Fresh | | Dry | |
| | | −P1 | +P1* | −P1 | +P1 | −P1 | +P1 |
| Uninoculated Control | | 9.8 | 3.6 | 1.34 | 0.75 | 0.074 | 0.034 |
| YCED 85 | 5.19 | 10.0 | 6.6[a] | 1.44 | 0.98 | 0.087 | 0.054[a] |
| WYE 27 | 3.02 | 10.0 | 5.0 | 1.54 | 0.72 | 0.090 | 0.039 |
| YCED 64 | 3.21 | 9.8 | 5.6[a] | 1.44 | 0.91 | 0.084 | 0.057[a] |
| WYEC 107 | 2.88 | 9.8 | 5.6[a] | 1.68[a] | 0.81 | 0.096[a] | 0.041 |
| WYE 41 | 1.18 | 10.0 | 4.2 | 1.45 | 0.73 | 0.087 | 0.047 |
| YCED 106 | 1.30 | 10.0 | 5.4[a] | 1.49 | 0.69 | 0.088 | 0.040 |
| YCED 71 | 5.25 | 10.0 | 6.2[a] | 1.42 | 0.85 | 0.082 | 0.050 |
| WYE 88 | 1.44 | 10.0 | 6.2[a] | 1.42 | 0.73 | 0.082 | 0.042 |
| MSSC 1 | 2.13 | 9.8 | 4.6 | 1.38 | 1.16[a] | 0.079 | 0.060[a] |
| WYE 21 | 9.56 | 10.0 | 6.6[a] | 1.49 | 1.09[a] | 0.091 | 0.059[a] |
| WYE 30 | 18.90 | 10.0 | 5.0 | 1.53 | 0.86 | 0.088 | 0.046 |
| WYE 28 | 0.18 | 10.0 | 3.6 | 1.39 | 0.90 | 0.079 | 0.049 |

P1* *P. ultimum*: 200 sproangia g$^{-1}$ dry potting mix. Where n = the average number of healthy plants per pot out of a total of 5 replicate pots of 10 plants.
[a]Significantly different from the corresponding control value at the P = 0.05 level.
Degrees of freedom = 100

In the absence of pathogens (denoted as "−P1" in Table IV) there were no significant differences between actinomycete-inoculated and control pots (without actinomycete) in the percentage of seeds geminating and producing healthy plants. Seed germination and outgrowth averaged ≧98% in all cases. However, the presence of the actinomycete sometimes delayed seed outgrowth by 1 to 3 days (data not shown). Similarly, in the absence of pathogens there were generally no significant differences between actinomycete-inoculated and control pots in plant shoot weight, measured either as fresh or dry weight. The exception was for pots inoculated with WYEC 107, where the presence of the actinomycete significantly enhanced the plant biomass yield.

In the presence of pathogen (+P1), the number of healthy plants per pot 20 days after planting averaged 3.6 of 10.0 in the control pots, as compared to 9.8 of 10.0 for control pots without pathogen. In the presence of specific actinomycetes, however, some significant improvements in the number of healthy plants were seen in pathogen-inoculated pots. Seven of the 12 actinomycetes (YCED 85, YCED 64, WYEC 107, YCED 106, YCED 71, WYE 88, AND WYE 21) significantly improved the yield of healthy plants. Of these, YCED 85, YCED 64, and WYE 21 also significantly improved plant dry weight yields relative to pathogen-only controls. WYE 21 also significantly improved fresh weight yields relative to pathogen-only controls. One strain that did not significantly improve the yield of healthy plants (MSSC 1) did improve both fresh and dry weight plant shoot yields (Table IV, columns 5 and 7). Thus, MSSC 1 may prove useful in protecting plants against lower doses of *P. ultimum* than used here.

EXAMPLE II

Isolation of Streptomyces WYEC 108

Strain WYEC 108 was identified as Streptomyces species on the basis of the morphological characteristics of the genus Streptomyces, as defined by Bergey's Manual of Systematic Bacteriology (1986). WYEC 108 is a filamentous bacterium that produces chains of spores in an aerial mycelium. As described above, Streptomyces WYEC 108 was isolated as one of a number of actinomycete strains isolated from soil taken from eight different sites in Great Britain. Along with other actinomycetes, Streptomyces WYEC 108 was isolated by the serial-dilution/spread-plate technique from rhizosphere soil associated with the roots of linseed plants in a field on Hastings Hill, South Downs, West Sussex, England. Dilutions ($10^{-5}$ to $10^{-7}$) of this soil were plated onto isolation agar medium WYE. Dilution plates were incubated at 25° C. for 4 to 10 days to allow actinomycete colonies to grow and sporulate. Then the colonies were picked and streaked onto WYEC agar plates for purification. Pure colonies of WYEC 108 were transferred from these plates to CYD agar slants, incubated at 25° C. until sporulated, and stored at 4° C. until used. Stock cultures were transferred every 3 to 4 weeks.

Identity of Streptomyces WYEC 108

As described above, the actinomycete strains isolated were examined for their ability to grow well and sporulate strongly on CYD agar. Subsequently, a number of isolates were tested for ability to inhibit the in vivo growth of the phytopathogen *Pythium ultimatum*. The isolates were also tested for in vitro antagonism against the white rot fungi *Phanerochaete chrysosporium* and *Coriolus versicolor* as well as the brown rot fungi *Postia placenta* and *Gloeophyllum trabeum*. As a result of these tests, one of these strains, herein referred to as Streptomyces WYEC 108 was selected based on its favorable characteristics.

Colonies of Streptomyces WYEC 108 grown on Casamino Acid/Yeast Extract/Dextrose (CYD) plates were examined by scanning electron microscopy. The sample preparation was as follows:
(1) colonies of Streptomyces WYEC 108 on CYD plates were covered with a 1.5% solution of glutaraldehyde in 0.2M sodium cacodylate buffer and fixed for at least two hours; (2) the colonies were completely washed (2×) with 0.2M sodium cacodylate buffer by aspirating the previous liquid with a pipette and replacing it with the buffer solution. Care was taken to insure that the sample did not dry out; (3) the colonies were then removed by taking "plugs" of agar, containing the colonies; (4) the "plugs" were placed into individual mesh containers and carried through dehydration in 100% ethanol (2×) (J. T. Baker Inc., Phillipsberg, N.J.); (5) the samples were then dried in a critical point drying "bomb" and mounted on individual specimen stubs using colloidal silver conducting paint. They were then coated with 60/40 gold-palladium and observed with a scanning electron microscope. Scanning electron photomicrographs showed the surface of the spores to be relatively smooth.

Various physiological characteristics of strain WYEC 108 were also determined: strain WYEC 108 did not produce melanin or $H_2S$ on Peptone-Yeast-Iron Agar and Peptone-Iron Agar (Difco Lab. Detroit, Mich.), respectively. The color of the spore mass produced by Streptomyces WYEC 108 on CYD plates was gray. This strain did not grow at 45° C. Streptomyces WYEC 108 may belong to the species *Streptomyces lydicus* or a related species, as defined by Bergey's Manual of Determinative Bacteriology (1986).

ATCC Accession Number

A deposit of Streptomyces WYEC 108 was made under the terms of the Budapest Treaty with the American Type Culture Collection (ATCC), Rockville, Md. on Jun. 29, 1993. This strain has been designated ATCC Accession No. 55445.

Preparation of Stock Cultures of Streptomyces WYEC 108

For short-term use, Streptomyces WYEC 108 was incubated on CYD agar or sporulation agar slant at 25° C. until sporulated and stored at 4° C. until used. For long-term storage of cultures, 10 ml spore suspensions were prepared by suspending spores from a single agar slant or plate in 10 ml sterile YGM medium. This spore suspension was then used to inoculate 250 ml Erlenmeyer flasks containing 100 ml YGM (yeast extract/glucose/mineral salts) medium. The flasks were then incubated with shaking at 250 rpm for 32–36 hours at 30° C. to provide a standard inoculum.

Samples from the YGM grown standard inoculum were also used for making glycerol cultures suitable for long-term storage at −70° C. and for lyophilization.

EXAMPLE III

In Vitro Antagonism of Fungal Phytopathogens by Streptomyces WYEC 108

The ability of Streptomyces WYEC 108 to inhibit the growth of a number of selected fungal phytopathogens was measured in terms of colony growth inhibition. Streptomyces WYEC 108 was streak-inoculated to one side of the center of corn meal agar (CMA) (Difco Lab., Detroit, Mich.) plates. Inoculated plates were incubated at 25° C. for about 8–12 days until the cultures had sporulated. Sporulation was detectable as a mass of grey aerial mycelium and spores by observation with the naked eye. Sporulation was observed by phase contrast microscopy (×1,000). A 5-mm-diameter CMA agar disc containing actively growing mycelium of a specific fungal phytopathogen was taken from the leading edge of a fungal culture and aseptically placed in the center of the agar plate. The plates were incubated at 25° C. until the test fungus reached the edge of a control plate not containing Streptomyces WYEC 108. Inhibition of fungal growth was quantified by determining the ratio of radial growth of fungal pathogen under the influence of Streptomyces WYEC 108 versus growth alone on the control plates. Percent inhibition of fungal growth was recorded after 48, 96, and 192 hr incubation depending on selected pathogenic fungus. The bioassay was replicated on five plates, inhibition was measured separately, and recorded as an average ±standard deviation.

The results of these in vitro bioassays are shown in Table V. This data shows that Streptomyces WYEC 108 exhibits very strong antagonism towards a wide range of fungal plant pathogens, including damping off (*Pyhthium ultimum*), root rot (*Pythium ultimum, Rhizoctonia solani, Fusarium solani*, and *Phytophthora cinnamomi*), white rot (*Phanerochaete chrysosporium* and *Coriolus versicolor*), brown rot (*Postia placenta* and *Gloeophyllum trabeum*) and leaf and stem rot (*Sclerotinia sp.*) fungi.

TABLE V

| Fungal pathogens | Percent inhibition ± standard deviation[a] Antagonism observed[b] | |
|---|---|---|
|  | 48 hr | 96 hr |
| *Pythium irregulare* | 100 ± 0.0 | 100 ± 0.0 |
| *Pythium ultimum* | 100 ± 0.0 | 100 ± 0.0 |
| *Rhizoctonia solani* | 100 ± 0.0 | 84 ± 0.0 |
| *Fusarium oxysporum* | 26 ± 2.5 | 26 ± 3.6 |
| *Fusarium sambucinctum* | 44 ± 2.4 | 35 ± 2.4 |
| *Fusarium solani* | 36 ± 2.5 | 19 ± 2.5 |
| *Phytophthora capsici* | 100 ± 0.0 | 100 ± 0.0 |
| *Phytophthora cinnamomi* | 100 ± 0.0 | 100 ± 0.0 |
| *Phytophthora parasitica* | 100 ± 0.0 | 100 ± 0.0 |
| *Sclerotinia cepivorum* | 100 ± 0.0 | 95 ± 1.5 |
| *Sclerotinia sclerotiorum* | 100 ± 0.0 | 100 ± 0.0 |
| *Phanerochaete chrysosporium* | 100 ± 0.0 | 100 ± 0.0 |
| *Coriolus versicolor* | 100 ± 0.0 | 100 ± 0.0 |
| *Postia placenta* | 100 ± 0.0[c] | 100 ± 0.0[d] |
| *Caldariomyces fumago* | 100 ± 0.0[c] | 100 ± 0.0[d] |
| *Gloeophyllum trabeum* | 100 ± 0.0[c] | 100 ± 0.0[d] |
| *Geotrichum candidum* | 47 ± 2.1 | 45 ± 2.1 |
| *Verticillium dahlias* | 73 ± 2.0[c] | 59 ± 2.0[d] |

[a]Values based upon averages of individual values of five replicated plates. Individual values were determined by separately measuring the mycelial growth from each plate.
[b]Inhibition of fungal pathogens defined as hyphal growth of pathogens under the influence of Streptomyces WYEC 108 versus growth alone on the control CMA plates.
[c]and [d]% inhibition at 96 hr and 192 hr incubation, respectively.

EXAMPLE IV

Use of Streptomyces WYEC 108 as a Seed Treatment

The efficacy of Streptomyces WYEC 108 cells to protect plants against phytopathogens was determined by applying strain WYEC 108 to ungerminated chickpea seeds and then planting these seeds in soil infested with the fungal phytopathogens *P. ultimatum* and *P. irregulare*.

Extracellular metabolites produced by strain WYEC 108 were extracted from cultures by ether extraction. The effect of these metabolites on fungal infection of emerging chickpea seedlings was also determined.

Growth of Streptomyces WYEC 108

For growth of strain WYEC 108 cells, one liter Erlenmeyer flasks containing 500 ml YGM (pH 7.1–7.2) were inoculated with 20 ml of stock culture and incubated with shaking at 250 rpm at 30° C. for 3 days for the production of cell mass. For production of antifungal metabolites, one liter Erlenmeyer flasks containing 500 ml CYD (pH 7.1–7.2) were inoculated with 20 ml of stock culture and incubated with shaking at 250 rpm at 30° C. for 7 days.

Treatment of Seeds with Streptomyces WYEC 108 and Antifungal Metabolites

A mycelial suspension of Streptomyces WYEC 108 was harvested by centrifugation at 5,000 rpm for 10 minutes from a 500 ml 3-day-old YGM liquid culture. The harvested mycelia were resuspended in 200–300 ml of sterilized 3% (w/v) sodium alginate solution to a culture density of $1.0–1.2 \times 10^4$ cfu/ml. Chickpea seeds were then added to the well mixed cell-alginate suspension and the seeds were transferred one by one into sterilized 0.25M $CaCl_2$ in distilled water. These seeds were used in the biocontrol assay described below.

Antifungal metabolites produced by Streptomyces WYEC 108 were obtained as follows. A 7-day-old 500 ml culture was filtered to remove cells and subsequently extracted with 150 ml ether using an extraction funnel. The ether was then removed by vacuum evaporation and the resulting extracts were redissolved in 1.5 ml distilled water. This solution was then filter sterilized through a sterile 0.45 μm filter and was added into 10 ml 3% (w/v) sodium alginate solution. The antifungal metabolite-alginate suspension was applied as described above to chickpea seeds for use in the biocontrol assay.

In Vivo Biocontrol Assay

Soil naturally infested with *P. ultimum* and *P. irregulare* is described in "Materials and Methods", above. This agricultural soil was used in this vivo biocontrol assays. Soil pH was determined to be pH 5.6 by thoroughly mixing a soil:water slurry (1:1), allowing the solids to settle for 2 h, and taking the pH of the supernatant solution. The soil was chopped, mixed thoroughly and then placed in seedling pots (10 cm deep×10 cm diameter).

The in vivo biocontrol assay was carried out by planting ungerminated chickpea seeds treated with either Streptomyces WYEC 108 or the antifungal metabolites in the infested soil. Untreated seeds planted in the same soil were used as a control. This procedure involved the following steps:

1) One cm of peat moss was placed in the bottom of each pot to prevent loss of soil while still providing for aeration and drainage.
2) Seedling pots were filled with the infested soil.
3) The soil was then watered to saturation from the bottom. After saturation of the soil surface, untreated and treated chickpea seeds were placed on the soil and covered 1.5–2.0 cm deep with the same soil. The topping was allowed to become wet by capillary action from the column of wet soil beneath. Ten seeds were planted in each of three replicate seedling pots. No fertilizer was added to the soil. To minimize drying and prevent crusting the pots were covered with clean plastic until seedling emergence. Additional water was sprayed on the top of the pots as needed, beginning after seedling emergence. Experiments were performed in a greenhouse at 15°–30° C. with a 12 hr light and 12 hr dark cycle photoperiod (16,000 lux).

Emergence counts of chickpea seedlings were made periodically, and final emergence counts were taken after 20 days. Emergence data were reported as the average for each treatment. The ability of Streptomyces WYEC 108 to act as a biocontrol agent was based on total emergence, plant height, and plant fresh weight, as compared to the control plants grown from untreated seeds with the biocontrol agent. The results of this biocontrol assay are shown in Table VI.

TABLE VI

| Treatment | Damping-off (%) Preemergence | Postemergence | Emergence (%) | Height (cm) | Fresh weight (g/plant) |
|---|---|---|---|---|---|
| Control | 86.7 | 6.6 | 6.7 | $4.3^a$ | $0.34^x$ |
| Streptomyces WYEC 108$^c$ | 36.7 | 0.0 | 63.3 | 11.3 | 1.05 |
| 3% Alginate$^d$ | 83.3 | 10.0 | 6.7 | $4.1^x$ | $0.32^x$ |
| Antifungal metabolites$^c$ | 63.3 | 3.3 | 33.3 | 8.9 | 0.66 |

$^c$In 3% alginate, coated on seeds.
$^d$Not containing WYEC 108.
$^x$Means so marked within column were not significantly different at the $P = 0.05$ level.

Both Streptomyces WYEC 108 cells and the antifungal metabolites produced by these cells reduced Pythium damping-off of the chickpeas.

Plants showed vigorous growth, when seeds were coated with Streptomyces WYEC 108 cells. There was a significant reduction in height and fresh weight of the plants that emerged from the control (untreated) chickpea seeds as compared to those of the plants germinated from seeds coated with Streptomyces WYEC 108 cells. Emergence of untreated chickpea seeds was extremely reduced (6.7% emergence) because of seed rot and preemergence damping-off disease caused by *P. ultimum* when seeds were planted in soil naturally infested with *P. ultimum* and *P. irregulare*. In contrast, emergence of seeds treated with Streptomyces WYEC 108 cells before seeding was 63.3%. Seeds treated with alginate alone did not show increased emergence. Symptoms typical of Pythium root rot, including root hair loss and root discoloration, were evident in harvested chickpea roots germinated from control seeds, but these symptoms were absent from plants grown from seeds treated with Streptomyces WYEC 108 cells. In the controls, damage to chickpea was mainly in the form of seed decay, and preemergence damping-off. Chickpea seedlings that did emerge and grow were stunted, and their roots were severely infected with *P. ultimum*. In a side by side comparison of chickpea plants taken from the biocontrol assay, the control plant, which was germinated from untreated seeds showed extensive root infection and lack of secondary roots and root hairs whereas the plants emerging from seeds coated with Streptomyces WYEC 108 showed good growth and normal formation of secondary roots and root hairs.

Emergence of chickpea seeds treated with antifungal metabolites in the form of ether soluble metabolite was higher (33.3%) than that of control seeds (6.7%), but lower than that of seeds coated with Streptomyces WYEC 108 cells (63.3%). Plants that emerged from seeds treated with antifungal metabolites showed vigorous growth, longer root, and a higher density of root hair development as compared to control plants.

EXAMPLE V

Effects of Streptomyces WYEC 108 on Root Infection and Seed Rot by *Pythium ultimum*

Chickpea seedlings grown as described in Example IV in soil naturally infested with *Pythium ultimum* and with and without pretreatment with WYEC 108 were examined to determine the effects of strain WYEC 108 on *P. ultimum* infection.

Root infection by *P. ultimum* was studied with control (untreated) chickpea seedlings harvested after 20-days of growth. *P. ultimum* causing root rot was also isolated from the rotted roots of these control plants. Isolation of *P. ultimum* was accomplished by first washing soil from the chickpea roots (rootlets and root hairs) with tap water and rinsing them twice with sterile distilled-water. Decolorized and rotted roots were cut out aseptically with a razor blade and placed on 3-day-old 2% water agar plates. The plates were incubated for 24–48 hrs at room temperature and observed under phase contrast microscope ($\times 40$). *P. ultimum* growing from the infected chickpea roots was subcultured to fresh 2% water agar and then identified as described previously (Ingram and Cook, 1990).

Seed rot by *P. ultimum* was studied with rotted control seeds harvested after 20-days. A part of a rotted seed was aseptically placed on 3-day-old 2% water agar plates with a sterilized toothpick, and incubated for 24–48 hrs at room temperature. The plates were examined as described above.

Pythium was observed to infect the roots of untreated chickpea plants growing in the naturally-infested soil. *P. ultimum* was the most prevalent species isolated from rotted seeds and roots. *P. irregulare* was less commonly observed.

Root colonization by Streptomyces WYEC 108 was examined in roots of 20-day-old chickpea plants that germinated from seeds treated with the Streptomyces WYEC 108 cell-alginate suspension described in Example II. These plants were grown in soil naturally infested with *P. ultimum* and *P. irregulare* also as described in Example II. The plants were removed from the seedling pots and gently washed with tap water to remove adhering rhizosphere soil. Then they were rinsed with sterile distilled-water. Root samples were prepared for microscopy by placing a portion of roots on a glass slide, adding a drop of methylene blue, and then covering this with a coverslip. Prepared samples were then observed with a phase contrast microscope ($\times 1000$).

Streptomyces WYEC 108 present on seeds came into contact with the emerging roots. As the roots elongated, the Streptomyces was carried along with the elongating root hairs and tips. Streptomyces WYEC 108 was observed to have extensively colonized the main root, secondary roots, root hairs and tips. Plants that emerged from seeds coated with Streptomyces WYEC 108 were healthier, had longer roots and root hairs were present in greater density than in control plants emerged from seeds not coated with the WYEC 108. This difference was clearly associated with colonization of the roots by the biocontrol agent. Roots colonized by the biocontrol agent did not show any symptoms of root diseases. Streptomyces WYEC 108 showed excellent root colonization in the presence of competition from the indigenous rhizosphere microflora.

EXAMPLE VI

Incorporation of Streptomyces WYEC 108 into Delivery Medium

A composition suitable for the long term storage of viable Streptomyces WYEC 108 spores and use in agricultural practices was formulated as follows. One liter Erlenmeyer flasks containing 500 ml YGM medium (pH 7.0–7.1) were inoculated with 20 ml of stock culture and incubated with shaking at 250 rpm at 30° C. for three days. After incubation, the culture was harvested by centrifugation at 5,000 rpm for 10 minutes. The harvested material was resuspended in 1600 ml of 10% YGM and mixed with sterilized 8 g $NH_4Cl$ dissolved in 400 ml distilled water. The two liters of cell and $NH_4Cl$ mixture were then inoculated into a plastic container containing 4 kg sterilized delivery medium consisting of a sand-water-cornmeal mixture in a 9-2-1 (w/w) ratio. The delivery medium was sterilized twice (3 hr at 121° C.) before incubation of the culture. This mixture was then incubated for 10–14 days at 25° C. to maximize the number of spores present in the mixture. Streptomyces WYEC 108 produced spores during the 10–14 days incubation resulting in increased cfu/g of delivery medium (to an average level of $10^8$ to $10^9$ cfu/g of delivery medium (dry weight). This mixture was then stored at 4° C. until use.

Alternatively, instead of YGM medium, cells and spores can be produced in CYG medium. As an alternative to harvesting cells by centrifugation, culture flasks may also be allowed to stand so that the bacterial mycelia and spores settle. Thereafter, the clear supernatant is decanted and the concentrated mycelia/spore suspension is inoculated directly into the delivery medium. When this harvesting procedure is utilized, it is not necessary to add $NH_4Cl$ to the medium since the bacterial growth medium (YGM or CYG) is a suitable source of nitrogen.

EXAMPLE VII

Influence of Streptomyces WYEC 108 on Emergence and Fresh Weight of Lettuce Seedlings To determine the effect of Streptomyces WYEC 108 on the growth of lettuce, lettuce seeds were grown either in the delivery medium containing Streptomyces WYEC 108 as described in Example VI above, or in steam sterilized soil. A total of 30 seeds was planted for each growth medium (one seed per 4×13.5 cm pot) and emergence was recorded after 21 days of growth. Fresh weight was determined by harvesting above ground plant growth after 35 days of growth. Fresh weight was recorded as a mean value. The results are shown in Table VII below.

TABLE VII

| Treatment | Number of Emerged Plant 7-day | 9-day | 21-day | Emergence (%) | Fresh weight (g/plant) |
|---|---|---|---|---|---|
| Sterile Soil + Seed | 13 | 17 | 21 | (21/30) 70 | 0.81 |
| Delivery Medium + WYEC 108 + Seed | 23 | 27 | 29 | (29/30) 97 | 1.41 |

These results indicate that treatment of lettuce seed with Streptomyces WYEC 108 enhances both the emergence frequency and fresh weight of the seedlings.

EXAMPLE VIII

Use of Streptomyces WYEC 108 in Delivery Medium in the Field

In vivo biocontrol assays were carried out to determine the effectiveness of Streptomyces WYEC 108 as a biocontrol agent when incorporated into the delivery medium described above.

Streptomyces WYEC 108 was produced and incorporated into the delivery medium as described in Example VII above, using Streptomyces WYEC 108 grown for three days in YGM medium. The initial population of Streptomyces WYEC 108 in the delivery medium was determined to be approximately $1.0-1.2 \times 10^5$ cfr/g of soil by plate counts on CYD plates immediately prior to planting seedlings in the pots. This treated soil was then used to fill seedling pots (4 cm by 13.5 cm).

Control plants were grown in pots containing steam sterilized soil (sterilized at 100° C. for 60 minutes).

Pepper seedlings (green, hot peppers) were then planted in the seedling pots containing either steam sterilized soil only or a mixture of steam sterilized soil inoculated with the delivery medium containing Streptomyces WYEC 108. After six weeks of growth in a greenhouse, these plants were transplanted to an agricultural field. In some instances, 100 g of the delivery medium containing 450 ±17 cfu/g of *Phytophthora parasitica* was inoculated into the planting hole prior to transplantation.

Plant height was determined 55 days after transplantation and recorded as a mean value. Plant biomass was determined by harvesting and measuring fresh weight of the plants after 110 days of cultivation post transplantation. At that time, the number of peppers formed and the weight of peppers per plant were recorded as a mean value. The results of this field trial are shown in Table VIII.

TABLE VIII

| Treatment | Plant Height (cm) | Biomass fresh weight (g/plant) | # of pepper per plant | Yield of pepper fresh weight (g/plant) |
|---|---|---|---|---|
| [b]Control: Untreated | 22.4k[y] | 274.1k[y] | 274.1k[y] | 158.8k[y] |
| [c]Treated with WYEC 108 | 29.1m | 353.3m | 36.5m | 279.8m |
| [b]Untreated + *P. parasitica*[d] | 20.3k | 238.5k | 13.8k | 151.2k |
| [c]Treated with WYEC 108 + *P. parasitica*[d] | 28.6m | 266.6k | 22.7k | 221.6k |

[b]Pepper plants grown in pots (4 cm × 13.5 cm) containing steam sterilized soil only.
[c]Pepper plants grown in pots containing a mixture of steam sterilized soil and delivery medium including Streptomyces WYEC 108.
[d]One hundred g of delivery medium containing *Phytophthora parasitica* was inoculated into individual hole before transplantation (450 ± 17 cfu/g of the delivery medium).
[y]Means in a column followed by the same letter are not significantly different at the P = 0.05 level.

As shown in Table VIII, treatment of pepper seedlings with WYEC 108 in the absence of *P. parasitica* produced statistically significant increases in plant height, biomass, number of peppers and yield of peppers compared to control plants that did not receive WYEC 108. A comparison of horizontal rows 3 and 4 of Table V shows that strain WYEC 108 protected peppers against the deleterious effects of *P. parasitica*. Additionally, there was a significant enhancement of the growth of plants treated with strain WYEC 108 in the absence of *P. parasitica* compared to untreated plants without *P. parasitica*.

EXAMPLE IX

Production of Spores of Streptomyces WYEC 108 in Liquid Media

Biocontrol agents must survive for extended periods of time to meet shipping needs and the timing patterns of agricultural uses. The use of spores of strain WYEC 108 rather than vegetative cells in particular biocontrol formulations enhances the shelf-life of the biocontrol formulation since the spores retain viability under adverse conditions and over long periods of time.

Typically, spores of Streptomyces species are only produced on solid media. However, as set forth below, the following method was found suitable for producing spores in liquid culture.

Two liter Erlenmeyer flasks containing 1,200 ml YGM medium (pH 6.5) were each inoculated with 50 ml of stock culture (produced as described in Example II) and incubated with shaking at 250 rpm at 30° C. for 12-18 days. Spore production in the culture was monitored by observing with phase-contrast microscope ($\times 1,000$, and stained with methylene blue). Conidiospores were harvested by centrifugation at 9,000 rpm for 10 minutes.

Thereafter, the conidiospores were resuspended in 1,600 ml of sterilized 10% YGM liquid medium and 400 ml of a sterile solution comprising 8 g $NH_4Cl$ in distilled water was added (to produce a final spore density of $1.0-1.2 \times 10^7$ cfu/ml). This mixture was then directly inoculated into 4 kg of sterilized delivery medium consisting of sand, water and cornmeal in a 9:2:1 (w/w) ratio. The delivery medium was sterilized twice in an autoclave (3 hours at 121° C.) prior to inoculation with the spores.

The production of spores directly in liquid culture in the described manner avoids the need for a further incubation of the mixture. The delivery medium containing spores was then stored at 4° C. until used.

Spores produced by the liquid culture method described were tested for viability after four months of storage at 4° C. One ml of spore suspension was inoculated into flasks containing 100 ml of sterilized 10% YGM liquid medium (pH 6.5) and incubated with shaking at 250 rpm at 30° C. Germination of spores was observed by phase-contrast microscopy ($\times 1,000$, stained with methylene blue). Spores were completely germinated in approximately 8 days. This simple observation test showed no loss in viability after this period of storage.

Streptomyces WYEC 108 incorporated into the delivery medium (sand, water, cornmeal; 9:2:1) was tested for viability as follows. A 1.0 g sample of the delivery medium containing Streptomyces WYEC 108 was serially diluted and plated on CYD agar plates. Plates were incubated at 25° C. until colonies were formed. An average level of $10^8$ to $10^9$ cfu/g of delivery medium (dry weight) were recorded with samples stored for 30 days.

Alternatively, the spores from an agar plate of sporulation agar were resuspended in 10-20 ml of sterile distilled water or YGM broth and mixed into 10-100 grams of delivery medium, to obtain a viable count of $10^{12}$ to $10^{14}$ cfu/g of medium. This mixture was then air-dried, mixed thoroughly and stored at 4° C. until used. This formulation is a concentrated product that can be diluted with additional delivery medium to any desired lower cfu/g final viable count.

EXAMPLE X

Stability of Alginate Gel Formulation

Mycelia of Streptomyces WYEC 108 were harvested by centrifugation at 5,000 rpm for 10 minutes from a 500 ml 3-day-old YGM liquid culture. The harvested mycelia were resuspended in 125 ml of 10% YGM and added 125 ml of sterilized 5% (w/v) sodium alginate solution to a culture density of $1.0-1.2 \times 10^4$ cfu/ml. Alginate pellets containing mycelia of Streptomyces WYEC 108 were formed by adding cell-alginate suspension drop by drop into sterilized 0.25M $CaCl_2$ in distilled water.

To determine the viability of the alginate pellets formed by this method, alginate pellets containing the culture were subsequently spread on a sterilized plastic petri dish (10 cm $\times$ 10 cm) and dried for one hour in a laminar flow sterile air hood. The pelletized Streptomyces WYEC 108 sporulated readily following storage at 25° C. for 6 to 8 months (to an average level of $10^8$ to $10^9$ cfu/g dried alginate beads). These spores were readily germinated when they were incubated in sterilized water at 25° C. Germination of the spores were observed by phase-contrast microscopy ($\times 1,000$ magnification, stained with methylene blue).

EXAMPLE XI

Preferred Formulation of Delivery Medium Including Streptomyces WYEC 108

Having set forth above methods for isolating actinomycete strains, testing these strains for utility as biocontrol agents, methods for producing these biocontrol agents in mycelial form and as spores, suitable delivery media and, in a preferred embodiment, Streptomyces WYEC 108, it will be apparent to one skilled in the art that the present invention can be modified in a number of ways without departing from the spirit of the invention.

Set forth below are examples of alternative embodiments of the present inventions, together with descriptions of particularly preferred embodiments.

Optimum Culture Conditions

Optimal conditions for growth of strain WYEC 108 include temperatures between 20° C. and 30° C., at pHs between 5.5 and 7.5, and at fermenter agitation speeds between 200 rpm and 300 rpm. Streptomyces WYEC 108 typically achieves maximal cell mass yields of about 5.3 dry weight grams of biomass/liter in YGM liquid medium with culture conditions of 30° C., pH 6.5, and shaking at 200 rpm for 72 hr (to the end of log phase). Doubling time during logarithmic growth phase is approximately 10 hours. The 72 hr incubation time may be significantly reduced by using higher inoculum levels of log phase cells.

Alternatively, spores may be produced on solid agar media such as sporulation agar. These spores may be directly harvested by scraping into a suitable liquid medium such as 10% YGM and then directly introduced into the delivery medium. This approach avoids the need for liquid growth of the culture and thereby shortens the production process.

Preferred and Alternative Delivery Media

Streptomyces WYEC 108 may be incorporated into a delivery medium for use in horticultural and agricultural settings. Example VI describes one formulation of the delivery medium which comprises sand-water-cornmeal in a 9-2-1 (w/w) ratio. It will be understood by one skilled in the art that the formulation of the delivery medium will be dictated by the particular application for which the biocontrol agent is intended. For example, various organic and inorganic fillers such as clay, vermiculite, wheat bran, corn cobs or chitin can be added to the delivery medium. The ratio of components of a delivery medium will be determined on the basis of texture and physical properties required. For example, properties such as moisture holding ability, light weight for easy handling and transportation, porosity to provide space for mycelial and plant root growth and spread may be important. Alternatively, vegetative mycelia or spores of Streptomyces WYEC 108 can be added to an alginate suspension to produce alginate-entrapped pellets on this strain. Methods of producing alginate pellets are known in the art and are described further in U.S. Pat. No. 4,668,512 to Lewis et al. Other ingredients, such as fertilizers, may also be incorporated into these pellets.

In a preferred embodiment, the present inventors have determined that a delivery medium comprising peat moss-sand-cornmeal in a 1:3.5:1 weight/weight ratio is particularly suitable. This ratio provides an appropriate density and water holding capacity for the use of this product in agricultural and horticultural applications. However, as stated above, other ratios of these components and of other components are also acceptable as delivery media. For example, an effective alternative delivery medium comprises peat moss (620 g)—sand (3380 g)—cornmeal (270 g)—chitin (10 g).

In one embodiment, approximately 1.6 liters of harvested culture broth (log-phase cells: e.g., about 72 hr culture) containing Streptomyces WYEC 108 mycelium grown in YGM broth as described above is supplemented with 400 ml of a sterile solution of $NH_4Cl$ (containing 8 g of $NH_4Cl$ in 400 ml distilled water) and inoculated into plastic containers containing 4 kg sterilized Delivery Medium consisting of peat moss, sand, and cornmeal. The Delivery Medium is sterilized twice (3 hours at 121° C.) before inoculation of Streptomyces WYEC 108. Inoculated containers are incubated at 30° C. for 10 to 14 days to maximize spore formation. Containers are then stored at 4° C. until used.

The use of $NH_4Cl$ in the delivery medium provides a nitrogen source of germinating spores of Streptomyces WYEC 108. It will be apparent to one skilled in the art that other nitrogen sources besides $NH_4Cl$ can be used for this purpose. For example, and as described herein, when spores are resuspended in bacterial growth medium (such as 10% YGM) prior to incorporation in the delivery medium, the addition of this nitrogen source is unnecessary. In preferred embodiments of the present invention, the delivery medium comprises a sufficient amount of a nitrogen source. It will be apparent to one skilled in the art that the determination of what comprises "a sufficient amount" of a nitrogen source can be made by determining the effects on germination frequency of increasing or decreasing the amount of a particular nitrogen source or the effects of changing the nitrogen source. A sufficient amount of a nitrogen source is that amount of a particular nitrogen source which facilitates germination of the spores or Streptomyces WYEC 108.

In an alternative embodiment, as described in Example XI, spores of Streptomyces WYEC 108 are produced in liquid medium and directly incorporated into the preferred delivery medium which is then stored at 4° C.

In a preferred embodiment of the present invention, Streptomyces WYEC 108 is added to the delivery medium to a final concentration of at least $1 \times 10^5$ cfu/g. In more preferred embodiments, the final concentration of Streptomyces WYEC 108 in the delivery medium is between $1 \times 10^5$ cfu/g and $1 \times 10^8$ cfu/g.

EXAMPLE XII

Detailed Description of Formulation of Delivery Medium Including Streptomyces WYEC 108

A preferred formulation of the delivery medium containing Streptomyces WYEC 108 is produced on a large scale by the procedure set forth below. All of the procedures described are performed using standard aseptic technique (e.g., in a UV light-sterilized laminar flow chamber) to assure asepsis until the packaged bags are opened by final users.

Production of Cells
1) Suspend the spores from a CYD slant of Streptomyces WYEC 108 in 10 ml of sterile YGM or CYG broth (pH 6.5). This inoculum suspension is used to inoculate the flask cultures.
2) Inoculate six 250 ml flasks containing 100 ml YGM (pH 6.5). Use 10 ml of spore suspension per flask as inoculum. After inoculation, flasks are incubated with shaking at 200 rpm and at 30° C. for about 36 hrs.
3) Inoculate six 2.0 liter flasks each containing 1.1 liter of YGM broth (pH 6.5) with the mycelial inoculum prepared above (100 ml of inoculum per flask). After inoculation, flasks are incubated with shaking at 200 rpm and at 30° C. for about 24 to 48 hrs or longer (up to 4 days). This becomes the inoculum for the fermenter.

Fermentation

Approximately 7.2 liter of the stock culture prepared above is inoculated into a fermenter containing 40 liter of sterile YGM broth (pH 6.5) (=a 15% inoculum by volume; the approach is to inoculate with as high a density of cell suspension as practical). The fermenter is operated with agitation (200 rpm) at 30° C. for about 72 hours (to near the end of log phase).

Fermenter Harvest
1) The fermentation culture broth containing the WYEC 108 cells (after about 72 hrs incubation) is aseptically harvested in sterile 20 liter plastic bottles.
2) Sterile $NH_4Cl$ solution is added to the harvested culture broth, which still contains the WYEC 108 cells (Use 16 g $NH_4Cl$ dissolved in 800 ml distilled water per 3.2 liter of harvested culture broth; pre-sterilized by autoclaving). The resulting 1.2 liter volume of $NH_4Cl$-containing cell suspension is then mixed well by shaking the bottle before it is inoculated into the previously prepared delivery medium.

Preparation of the Delivery Medium
1) Each component of the Delivery Medium is measured separately and added into a large size sterilizable pan or other suitable container. The combined mixture is defined as the delivery medium. It consists of peat moss, sand, and cornmeal (540 g:2700 g:540 g; 1:3.5:1 w/w ratio).
2) The delivery medium is thoroughly mixed and covered with sturdy aluminum foil or cotton batting and then sterilized twice (90 minutes at a time at 121° C. with 12 hours between sterilization periods).

3) The delivery medium is cooled to room temperature after the second sterilization and before inoculation of the harvested culture broth containing strain WYEC 108 and NH₄Cl solution (prepared above).

Incorporation of Streptomyces WYEC 108 into the delivery medium to Create a Formulation of Peat Moss, Sand, Water, Cornmeal, and NH₄Cl 1) About 0.5 liters of harvested culture broth containing strain WYEC 108-NH₄Cl solution (prepared above) is thoroughly incorporated into each of as many as needed presterilized plastic containers containing of 3.78 kg of delivery medium.

2) The inoculated containers are then incubated at 30° C. for 10–14 days (up to 20 days incubation may be optimal) after which they can be stored at 4° C. until used (the formulation is stable for months).

Handling and Transportation

1) The completed formulation containing Streptomyces WYEC 108 is aseptically transferred into sterile triple-layer plastic bags using a small sterilized shovel or equivalent tool, preferably in a UV-sterilized laminar flow hood.

2) The filled bags are next tied and put into 1.5 ft³ moving boxes for shipping. Each box is then sealed with strong tape.

EXAMPLE XIII

Incorporation of the Formulation Containing Streptomyces WYEC 108 into Seedling Nursery Beds The formulation containing the Streptomyces WYEC 108 biocontrol agent and delivery medium as described in Example XII is mixed with a nursery bedding soil or potting mix to a final Streptomyces concentration of $\geq 1.0$–$1.2 \times 10^5$ or more cfu/g-soil). The seedling procedure is as follows.

1) About 1.0 cm of peat moss is placed in the bottom of each pot (or bed) to prevent loss of soil (or potting mix) while still providing for aeration and drainage.

2) Seedling pots are then filled with the agricultural (nursery or potting mix) soil up to about 3.0 cm below from the top of the pots (or beds). The pots (beds) are then watered to saturation.

3) About 1.5 cm of the formulation containing Streptomyces WYEC 108 and delivery medium is then added to the top of each pot (bed). If desired, the formulation can also pre-mixed with nursery bedding soil or potting soil to increase the volume and adjust the cfu/g count. However, for optimum efficacy, the cfu/g should be maintained at at least $10^5$ cfu/g in the final mix.

4) Seeds are placed on the surface of the prepared seedling pots or beds and then covered with an additional 1.5 cm (approximate) of nursery bedding soil or potting soil/mix.

5) A small amount of water is then added to wet the soil and seeds.

6) To minimize drying and to prevent crusting, the pots are typically covered with clean black plastic until seedling emergence (This may not necessary if moisture is controlled).

7) Additional water is sprayed on the top of the pots (or beds) as needed after seedling emergence.

Having provided examples of embodiments of this invention and preferred embodiments, it will be apparent to those skilled in the art that changes and modifications may be made without departing from the present invention and its broader aspects. We therefore intend the appended claims to cover all such changes and modifications falling within the true spirit and scope of the present invention.

REFERENCES

ATCC Catalogue of Bacteria and Bacteriophages, 17th Edition, 1989. Amterican Type Culture Collection, Rockville, Md.

Locci, R. 1989. "Streptomycetes and Related Genera," in Bergey's Manual of Systematic Bacteriology, Williams and Wilkens, Baltimore, Md. 4:2451-2492.

Filnow, A. B. and J. L Lockwood. 1985. Evaluation of several actinomycetes and the fungus *Hypochytrium catenoides* as biocontrol agents of Phytophthora root rot of soybean. Plant Disease 69:1033-1036.

Ingram, D. M. and R. J. Cook. 1990. Pathogenicity of four Pythium species to wheat, barley, peas, and lentils. Plant Pathology 39:110-117.

Kraft, J. M. and D. W. Burke. 1971. *Pythium ultimum* as a pathogen of beans and peas in Washington. Plant Dis. Rep. 55:1056-1060.

Lynch, J. M., R. D. Lumsden, P. T. Atkey, and M. A. Ousley. 1992. Prospects for control of Pythium damping-off of lettuce with Trichoderma, Gliocladium, and Enterobacter spp. Biol. Fertil. Soils 12:95-99.

Lynch, J. M., K. L. Wilson, M. A. Ousley, and J. M. Whipps. 1991. Response of lettuce to Trichoderma treatment. Lett. Appl. Microbiol. 12:59-61.

Miller, J. J. E. Liljeroth, G. Henken, and J. A. van Veen. 1990. Fluctuations in the fluorescent pseudomonad and actinomycete populations of rhizosphere and rhizoplane during the growth of spring wheat. Can. J. Microbiol. 36:254-258.

Pridham, T. G. and D. Gottlieb. 1948. The utilization of carbon compounds by some actinomycetales as an aid for species determination. J. Bacteriol. 56:107-114.

Reddi, G. S., and A. S. Rao. 1971. Antagonism of soil actinomycetes to some soil borne plant pathogenic fungi. Indian Phytopathol. 24:649-657.

Stanghellini, M. E. and J. G. Hancock. 1970. A Quantitative Method for the Isolation of *Pythium ultimum* from Soil. Phytopathology. 60:551-552.

Stasz, T. E., G. E. Harman and G. A. Marx. 1980. Time and site of infection of resistant and susceptible germinating pea seeds by *Pythium ultimum*. Phytopathology. 70:730-733.

Trapero-Casas, A., W. J. Kaiser and D. M. Ingram. 1990. Control of Pythium seed rot and preemergence damping-off of chickpea in the U.S. pacific northwest and Spain. Plant Dis. 74:563-569.

Westerlund, F. V., Jr., R. N. Campbell and K. A. Kimble. 1974. Fungal root rots and wilt of chickpea in California. Phytopathology 64:432-436.

We claim:

1. A biologically pure culture of a microorganism Streptomyces WYEC 108, having the identifying characteristics of ATCC 55445.

2. The microorganism of claim 1 wherein the microorganism is capable of conferring protection against fungal infection in a susceptible plant.

3. The microorganism of claim 2 wherein protection is conferred against fungal pathogens that cause damping-off, root rot, brown rot and white rot.

4. A composition comprising:
- a biologically pure culture of Streptomyces WYEC 108; and
- a delivery medium.

5. The composition of claim 4 wherein the delivery medium comprises alginate gel.

6. The composition of claim 4 wherein the delivery medium comprises peat moss.

7. The composition of claim 4 wherein the delivery medium comprises sand.

8. The composition of claim 4 wherein the delivery medium comprises cornmeal.

9. The composition of claim 4 wherein the delivery medium comprises a sufficient amount of a nitrogen source.

10. The composition of claim 4 wherein the delivery medium comprises peat moss, sand, cornmeal and a sufficient amount of a nitrogen source.

11. The composition of claim 10 wherein the nitrogen source is ammonium chloride.

12. The composition of claim 4 wherein the biologically pure culture of Streptomyces WYEC 108 comprises spores.

13. A composition capable of protecting plants against fungal infection comprising Streptomyces WYEC 108 and a delivery medium in a suitable container.

14. The composition of claim 4 wherein the composition is capable of reducing fungal infection of a susceptible plant when administered to the roots of said plant.

15. A method for reducing the susceptibility of a plant to fungal infection wherein the method comprises delivering Streptomyces WYEC 108 to the roots of the plant.

16. A method for reducing the susceptibility of plants to fungal infection wherein the method comprises the steps of:
- immersing plant seeds in a composition comprising Streptomyces WYEC 108; and
- planting the seeds in a suitable growth medium.

17. The method of claim 16 wherein the composition further comprises alginate gel.

18. A method of protecting plants against fungal infection comprising the steps of:
- supplying a culture of Streptomyces WYEC 108;
- preparing a delivery medium comprising said culture; and
- delivering said delivery medium to plants.

19. A method of enhancing the growth of plants comprising:
- providing a growth medium containing Streptomyces WYEC 108; and
- planting plant seedlings or seeds in said growth medium.

20. A method for enhancing the germination frequency of plant seeds wherein the method comprises the steps of:
- immersing plant seeds in a composition comprising Streptomyces WYEC 108; and
- planting the seeds in a suitable growth medium.

* * * * *